(12) United States Patent
Herzog et al.

(10) Patent No.: US 11,096,697 B2
(45) Date of Patent: Aug. 24, 2021

(54) FIBULA BONE MATERIAL REMOVAL AND TRANSFER TEMPLATE

(71) Applicant: KARL LEIBINGER MEDIZINTECHNIK GMBH & CO. KG, Mühlheim (DE)

(72) Inventors: Rebecca Herzog, Mühlheim (DE); Lorenz Gabele, Mühlheim (DE)

(73) Assignee: KARL LEIBINGER MEDIZINTECHNIK GMBH & CO. KG, Muhlheim (DE)

( * ) Notice: Subject to any disclaimer, the term of this patent is extended or adjusted under 35 U.S.C. 154(b) by 277 days.

(21) Appl. No.: 16/093,752

(22) PCT Filed: May 2, 2017

(86) PCT No.: PCT/EP2017/060432
§ 371 (c)(1),
(2) Date: Oct. 15, 2018

(87) PCT Pub. No.: WO2017/191139
PCT Pub. Date: Nov. 9, 2017

(65) Prior Publication Data
US 2019/0076154 A1    Mar. 14, 2019

(30) Foreign Application Priority Data
May 6, 2016    (DE) ............ 10 2016 108 426.3

(51) Int. Cl.
*A61B 17/15*    (2006.01)
*A61B 17/80*    (2006.01)

(52) U.S. Cl.
CPC ............ *A61B 17/152* (2013.01); *A61B 17/15* (2013.01); *A61B 17/8071* (2013.01)

(58) Field of Classification Search
CPC .......... A61B 17/15; A61B 17/151–158; A61B 17/16; A61B 17/152; A61B 17/8071
(Continued)

(56) References Cited

U.S. PATENT DOCUMENTS

2012/0029646 A1    2/2012  Fernandes
2013/0296872 A1*  11/2013  Davison ............... A61B 17/151
                                                        606/87
(Continued)

FOREIGN PATENT DOCUMENTS

CN    104507403 A    4/2015
CN    104825235 A    8/2015
(Continued)

OTHER PUBLICATIONS

German Office Action, DE 10 2016 108 426.3, dated Dec. 16, 2016 (English translation attached) (8 pp.).
(Continued)

*Primary Examiner* — Jessica Weiss
(74) *Attorney, Agent, or Firm* — Eversheds Sutherland (US) LLP

(57) ABSTRACT

The disclosure relates to a fibula bone material removal and transfer template including a center part with a central body each end of which has a separating tool guide portion, at least one of the bone separating tool guide portions being mounted such that it can be moved away from and pushed towards the center part.

7 Claims, 14 Drawing Sheets

(58) Field of Classification Search
USPC .............. 606/70–71, 280–299, 87–89, 86 R
See application file for complete search history.

(56) References Cited

U.S. PATENT DOCUMENTS

| | | | |
|---|---|---|---|
| 2013/0304075 A1 | 11/2013 | Tseng et al. | |
| 2013/0338779 A1 | 12/2013 | Fernandes | |
| 2014/0149095 A1 | 5/2014 | Davison et al. | |
| 2016/0296290 A1 | 10/2016 | Furrer et al. | |
| 2018/0360477 A1* | 12/2018 | Singh ................. | A61B 17/1728 606/87 |
| 2019/0076154 A1 | 3/2019 | Herzog et al. | |

FOREIGN PATENT DOCUMENTS

| | | |
|---|---|---|
| DE | 696 36 636 T2 | 8/2007 |
| DE | 69636636 T2 | 8/2007 |
| DE | 210 2016 108 426 A1 | 9/2017 |
| EP | 0 809 471 B1 | 10/2006 |
| JP | 201551732 A | 6/2015 |
| RU | 182 499 U1 | 8/2018 |
| WO | 2004039266 A1 | 5/2004 |
| WO | WO-2004039266 A1 * | 5/2004 ........... A61B 17/152 |
| WO | 2013/165559 A1 | 11/2013 |

OTHER PUBLICATIONS

International Search Report and Written Opinion, PCT/EP2017/060432, dated Jul. 27, 2017 (in German) (12 pp.).
International Search Report, PCT/EP2017/060432, dated Jul. 27, 2017 (in English) (2 pp.).
Chinese Office Action, 201780027909.8, dated Nov. 3, 2020 (with English translation) (13 pp.).
Russian Search Report, DE 2016 108 426.3, dated (in Russian) (2 pp.).
Russian Office Action, Application No. 2018141609/14, dated Sep. 23, 2020 (English translation attached) (19 pp.).
Japanese Office Action, 2018-554778, dated Mar. 10, 2021 (with English translation) (12 pp.).

* cited by examiner

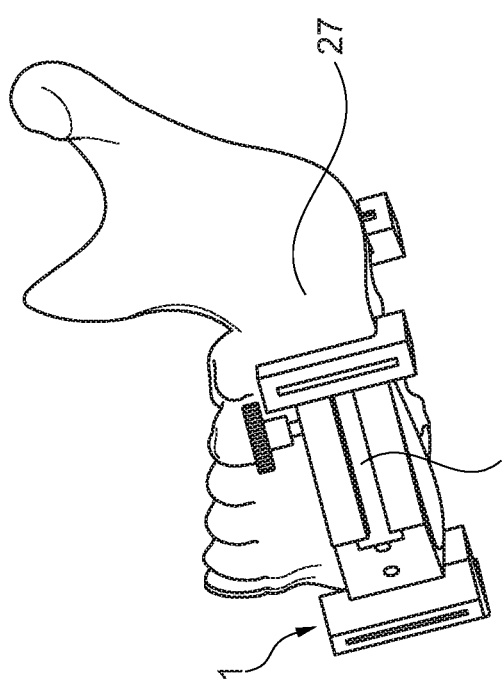
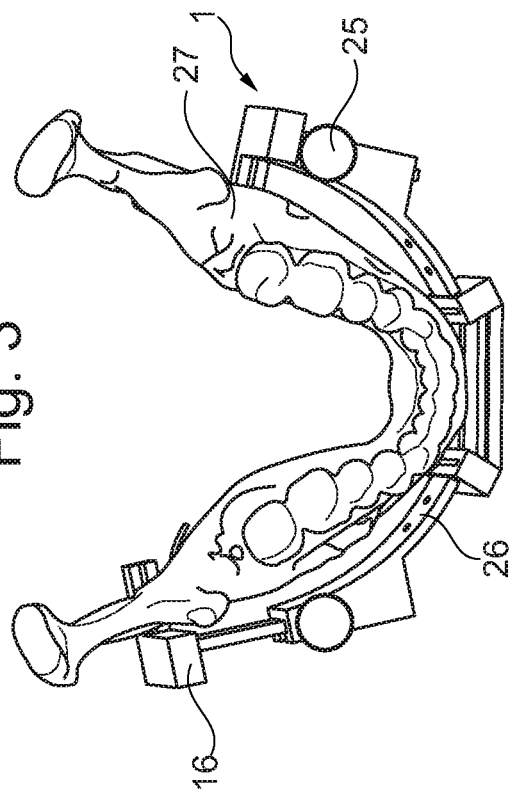
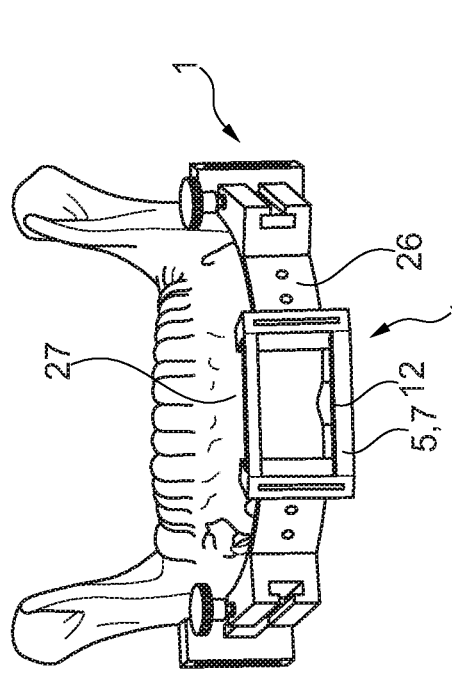
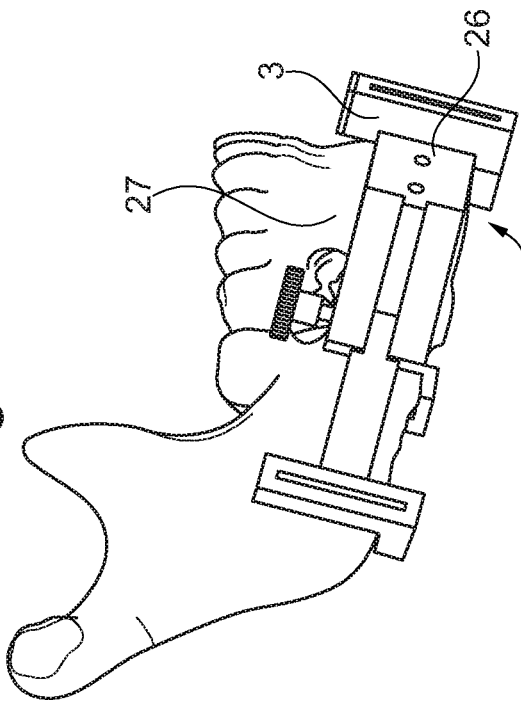

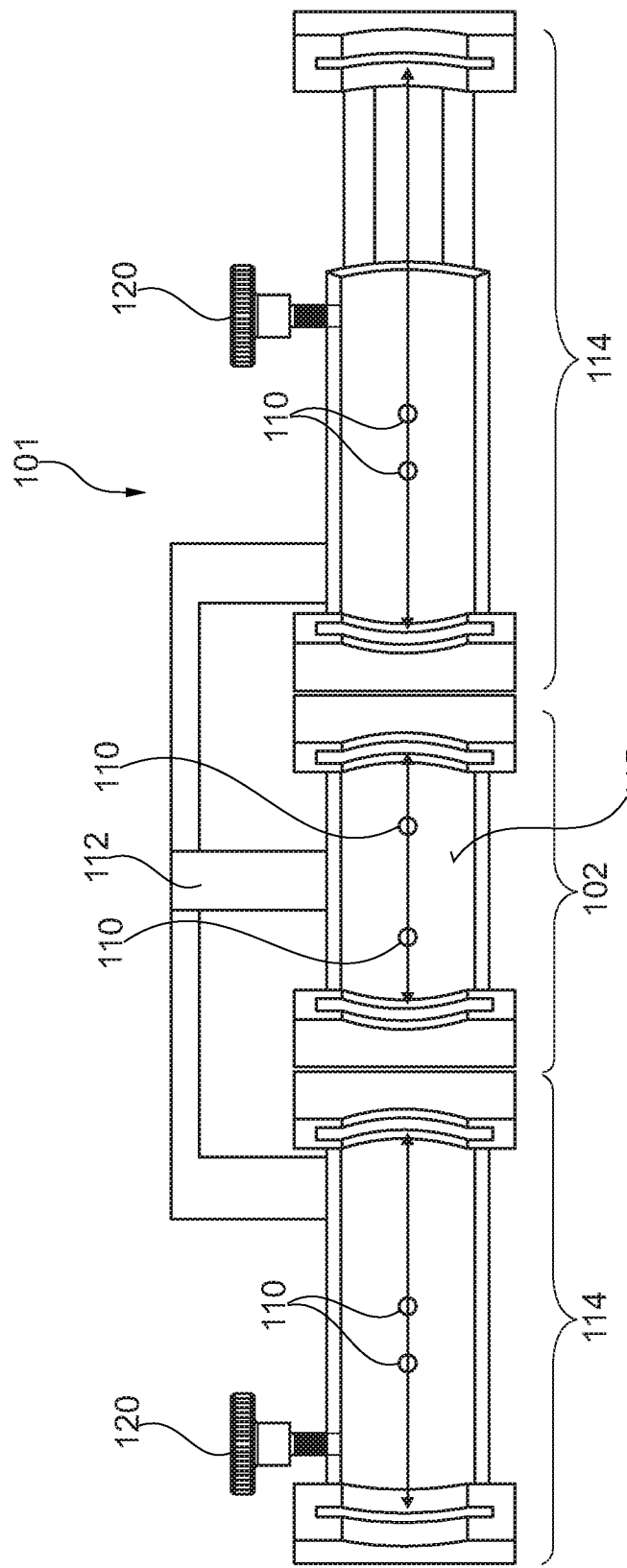

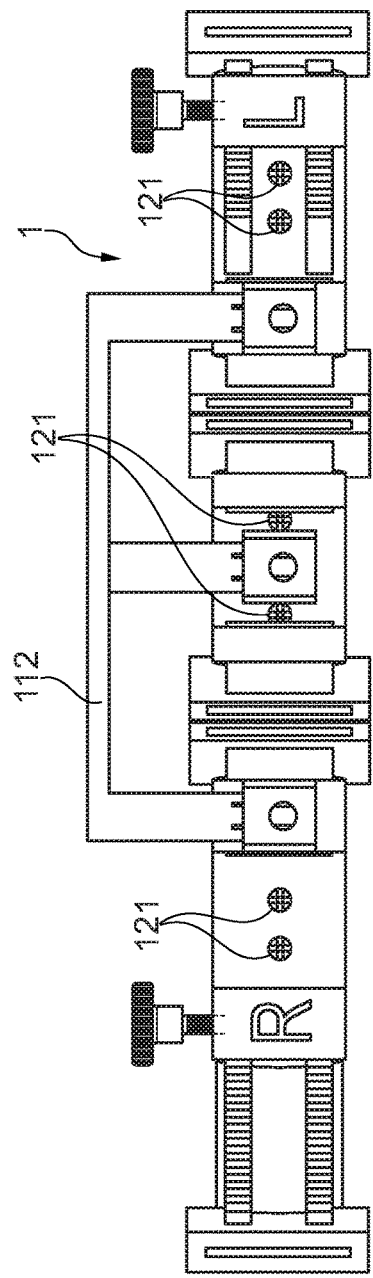
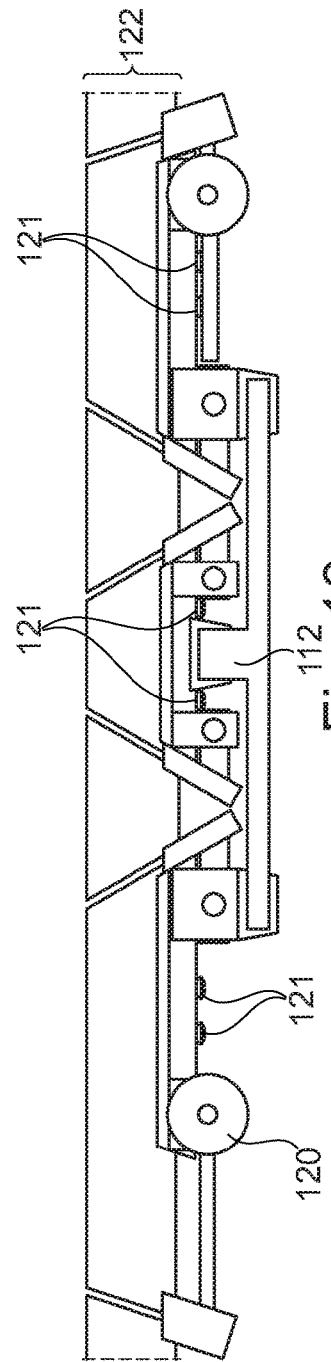
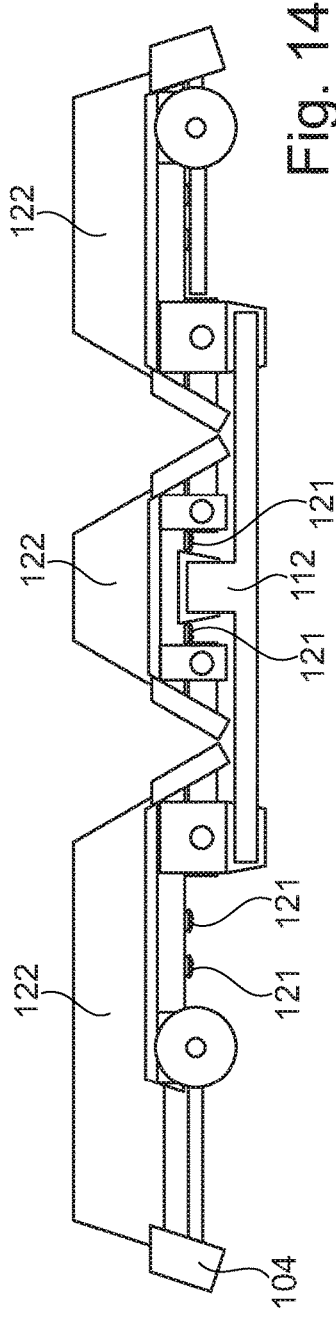

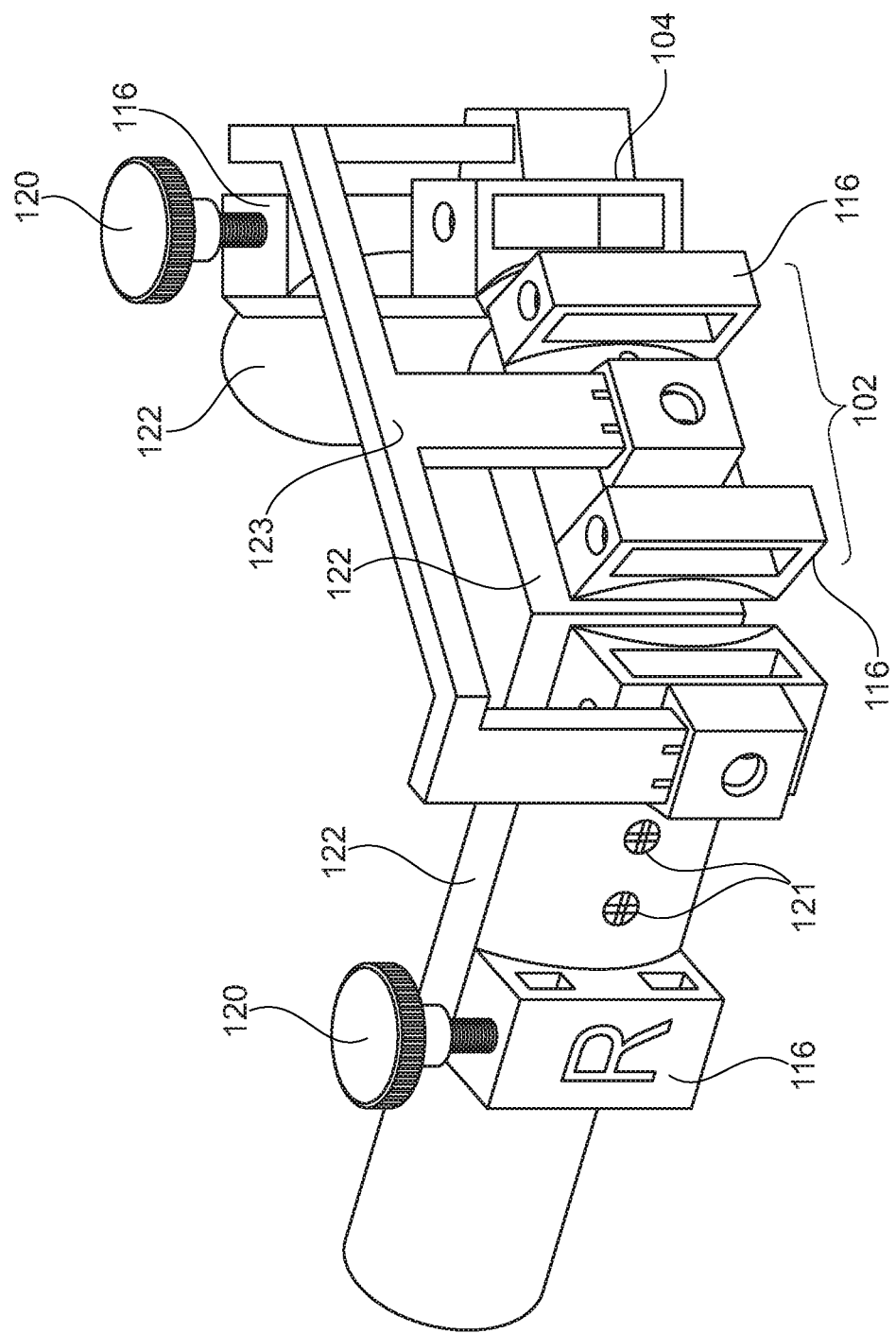

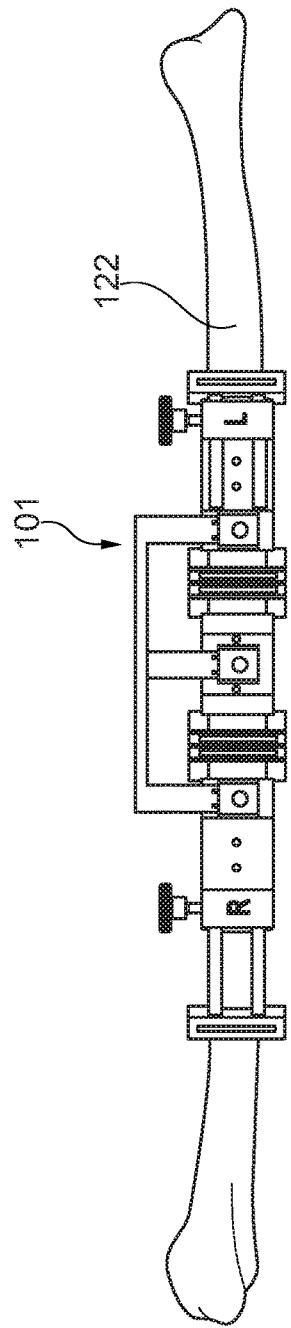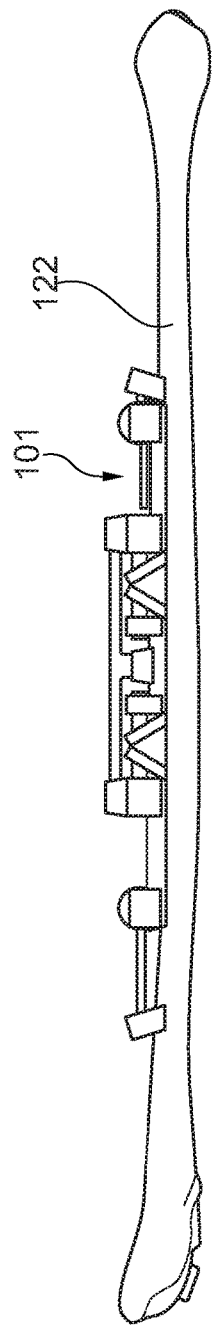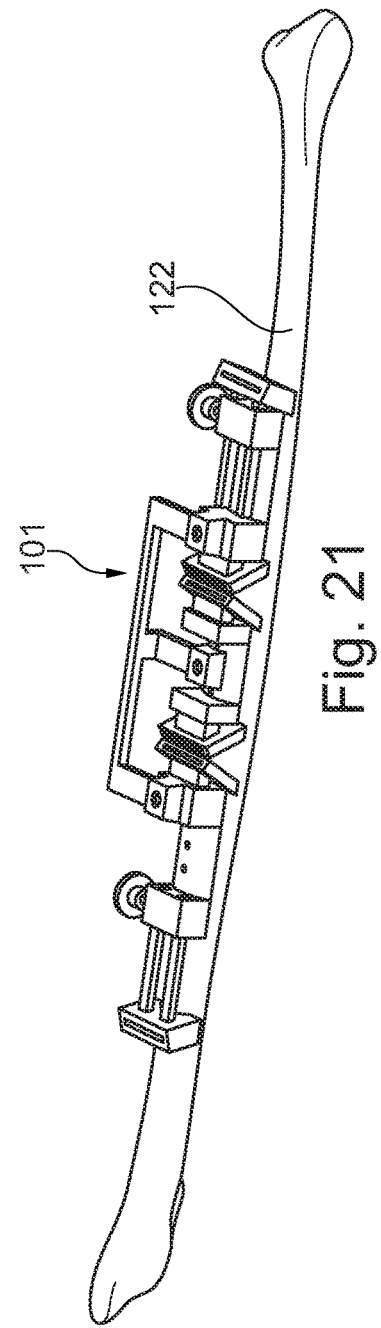

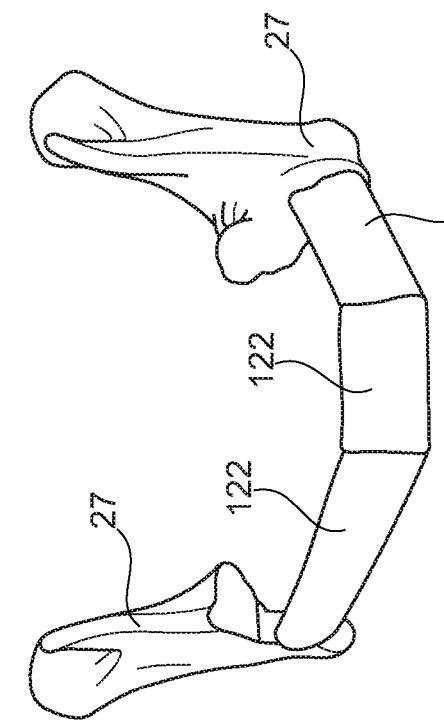
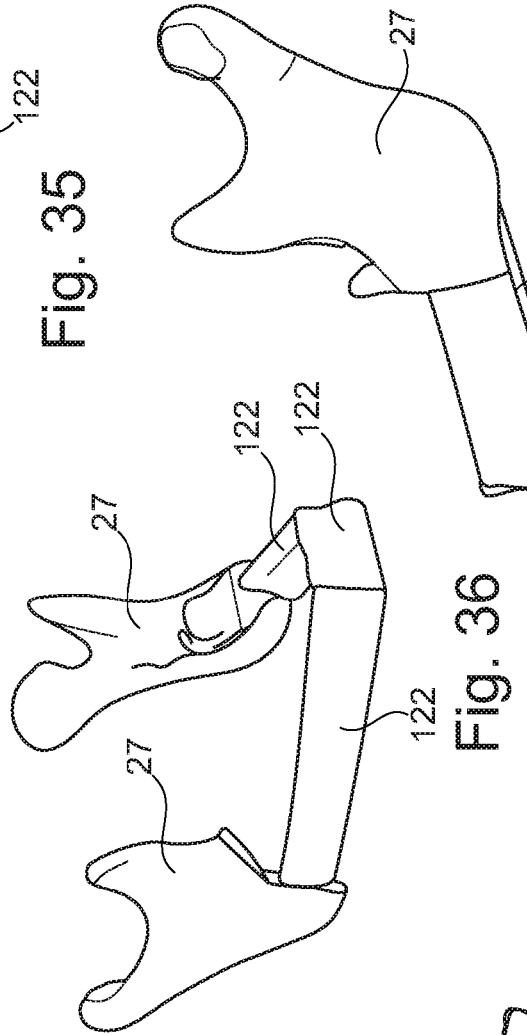
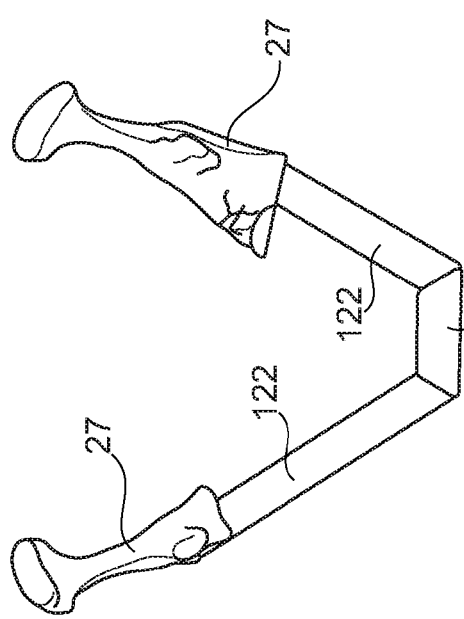
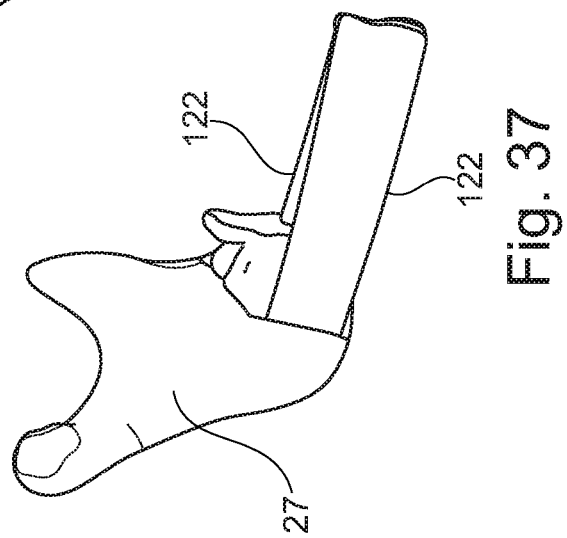

FIBULA BONE MATERIAL REMOVAL AND TRANSFER TEMPLATE

TECHNICAL FIELD

The invention relates to a fibula bone material removal and transfer template comprising a center part with a central body each end of which has a bone separating tool guide portion.

BACKGROUND OF THE INVENTION

From the state of the art, sawing templates such as mandibular resection templates are known already. For example, WO 2004/039266 A1 discloses a sawing template which is adapted to be used on a fibula or a mandibula. Similar devices are also known from US 2012/0029646 A1, US 2013/0338779 A1 and US 2013/0304075 A1.

Sometimes for example human lower jaw bones such as a mandible are damaged by accident or carcinogenic modifications such that parts of said bones have to be removed. The bone then has to be recompleted. Recently, it has been started to insert bone portions that were removed e.g. from a fibula, viz. a calf bone, to the position freed from the defect/the blank of the mandible again. Here it is required to perform precise cuts in a predetermined manner both on the mandibular bone and, corresponding thereto, on the fibula.

To this end, usually mandibular resection templates are used which are in charge of precise cutting on the mandible, just as fibula bone material removal and transfer templates which are in charge of precise cuts on the fibula and, at the same time, are used for precise transfer of the resected bones for implantation in the mandibular area.

The previously known solutions are not sufficiently precise, though they are very complicated to handle. Also, they are relatively cost-intensive. In this respect, improvements are intended to be achieved.

SUMMARY OF THE INVENTION

Hence, it is the object of the present invention to eliminate or at least alleviate the drawbacks of the state of the art and to make available a fibula bone material removal and transfer template which can be used so as to achieve an esthetically and mechanically appealing result in the mandibular area, especially utilizing an improved mandibular resection template.

In some cases, a particular patient-specific template is manufactured for mandibles. This is very cost-intensive and time-consuming, however; therefore, the approach of the present invention resides in making available a universal mandibular resection template which is finally adapted to a representative patient out of the crowd of all potential patients.

Ergo, in a side aspect especially universal templates for resection of the mandible, but in a main aspect of the fibula—with an oncoming mandible reconstruction of the microvascular fibula transplant as well as a system of mini-plates for fixing the transplant adapted to this technique—are to be made available.

This object is achieved with a generic fibula bone material removal and transfer template by the fact that at least one of the bone separating tool guiding portions, preferably both bone separating tool guide portions, can be moved away from the center part, is/are especially mounted to be moved away or pushed towards the center part. In particular, rotary and pivoting bearings might be suited in this case. It is aimed at obtaining such bearing that the miters of the bone portions are made to be abutting for mounting in the mandibular area, for example.

A fibula bone material removal and transfer template of this type which is already substantially improved can even be further improved. Said further enhancements are claimed in the subclaims and shall hereinafter be illustrated in detail.

So, it is of advantage when the bone separating tool guide portion has a guide slit formed between two vertical surfaces which is open on the front and rear sides thereof. In this way, when removing bone from the fibula the bone separating tool is prevented from deflecting. This ensures precise removal.

It is beneficial to the handling when the guide slit is open on the lower side and/or the upper side thereof.

The adjustability and flexibility during use/during operation is improved when a beam which is movably supported in a guide path encompassing the same along its longitudinal direction projects from the bone separating tool guide portion separate from the center part.

It is also expedient when a fixing screw designed for securing the beam protrudes into the guide path. Then intra-operatively a simple change can be carried out or can be prepared at least pre-operatively.

It has proven itself when approximately in the middle of the center part a bracket receiving device such as a clip is present into which an auxiliary resection bracket can be or is inserted. The individual component parts of the fibula bone material removal and transfer template then can be fixed invariably relative to each other in space.

It is of advantage when in the bracket receiving device a hole such as a blind hole or a through-hole is present which is prepared for receiving a spring portion fixed to the auxiliary resection bracket by locking. This enables quick insertion and removal of the auxiliary resection bracket.

It has also proven itself when a receiving hole for a bone screw is provided on both sides of the clip.

It is beneficial to proper attachability when the receiving hole has an axis of symmetry that is orientated transversely, preferably perpendicularly, to a central plane receiving the central body.

It is also beneficial to flexible operative use when on either or each of the two bone separating tool guide portions a supplementary component is present on the side facing away from the central body. Furthermore, it is advantageous when at the distal end of the supplementary component another bone separating tool guide portion is arranged to be displaceable and removable from the supplementary component.

One advantageous exemplary embodiment is also characterized in that the bone separating tool guide portions of the supplementary component are identical to or at least similar to the bone separating tool guide portions of the central body.

One advantageous exemplary embodiment may also be designed such that at the bone separating tool guide portion configuration present at the distal free end of the supplementary component there are provided two guiding webs which are guided within separate openings in a joint guide block.

When one, two or more set screw(s) contacting only the upper guiding web is/are inserted in the guide block, an easily accessible area for locking and releasing the locking can be chosen/used. Preferably, the set screw is not detachable.

It has also proven itself when a screening or notch is provided on either or both of the guiding webs, especially on the front side by ribs extending transversely, preferably orthogonally, to the longitudinal direction of one guiding web or both guiding webs. In such case, haptic feedback to the operating surgeon can be relatively easily realized.

It is of advantage when a bracket receiving device for receiving the auxiliary resection bracket by locking is present on the supplementary component. In order to improve the survey for the segment picture onto the brackets, the segments are marked with "R" for right and "L" for left.

One advantageous exemplary embodiment is also characterized in that the bracket receiving device of the supplementary component is formed identically or at least similarly to the bracket receiving device of the central body.

It has also proven itself when the two supplementary components are formed mirror-symmetrically to an axis of symmetry extending centrally through the central body and being vertically penetrated by the latter.

It is of advantage when the auxiliary resection bracket has at least two or four (90°) steps. This helps to avoid deformation of soft tissue.

It is beneficial to the invention when the rear side of the template is prepared for contacting a (human) fibula.

It is desirable when the two guide slits at the central body enclose an angle of about 60°+/−5° and/or the two guide slits of the supplementary component enclose an acute angle such as an angle of about 72°+/−5° in the direction of the rear side.

Accordingly, it is advantageous when the bracket receiving devices are prepared for receiving a rigid/stiff/non-elastic/dimensionally stable (similarly to a steel component) auxiliary implanting bracket. In this way, the individual bone pieces can be displaced true to position.

When the auxiliary implanting bracket is identical or similar to the auxiliary resection bracket but differs by the position imposed on the supplementary component and the central body relative to each other, ergo has a configuration which is geometrically different at the connection sites, transfer of the bones resected from the fibula to the mandible with its respective gaps can be efficiently realized.

Furthermore, it is of advantage when the auxiliary resection bracket forces the supplementary component and the central body into a joint plane, but the auxiliary implanting bracket forces the supplementary component and the central body into a U-shape and/or an orientation consistent with the mandibular contour.

The fibula bone material resection and transfer template may also be referred to as fibula resection template and is adapted to the average shape of the fibula. Hence, it is not patient-specific but is adapted to the average patient.

The individual segments and lengths are adapted to the mandibular resection template. The scales of the two templates should be uniformly designed and adapted to each other. However, the preoperative planning need not absolutely be taken into consideration.

The individual segments are connected to each other by a removable bracket. The bracket is intended to be attachable both from the top and from the bottom so as to use the template equally for the right and left fibulae. Moreover, the bracket is to be provided with a small step so that it projects further forward, as this area is frequently obstructed by soft tissue. In addition, the removable bracket is designed to be elastic. That is, the individual segments fit tightly to the fibula so that the separating cuts/sawing cuts can be carried out exactly at an angle.

The set screws for locking the flexible slits are preferably intended to be arranged orthogonally to the template.

For carrying out the resection an oscillating saw is to be used. It is being considered to design the guide slit/saw slit about 1.0 mm in width to be open downwards or upwards or on both sides or to be closed. However, in any case there should be a lateral guidance of the saw blade.

The template is fixed to the fibula by standard screws having an outer diameter of about 2.0 mm. In each segment two bores are located for fixations.

The template should at its best enable fixation of the resected fibula segments by means of implants from the front. Therefore, a recess is provided at each segment. At present, each of the right and left segments is connected to the front segment by a plate curved at an angle of about 120°. The plate is arranged from above.

Mini-plates having a profile of 1.0 mm which allow for simple transplant fixation and are pre-shaped up to a three-dimensional shape by way of the average shape of the mandible and, resp., the fibula transplant have stood the test. The contours of the average mandible as well as of the fibula are generated on the basis of representative data sets.

The plates have to be made available in different forms and configurations. It is aimed at getting along with as few plates as possible. The exact variants then still have to be established in all. However, four-hole plates including a web and/or six-hole plates including a web are imaginable. The plates should have multi-directional angularly stable plate holes so that they both can be blocking and interact with standard screws. Depending on necessity, specific instruments may be used to fix the plate, for example screw drivers.

The invention also relates, in a side aspect, to a mandibular resection template, comprising a central component which is prepared for being attached to a segment, such as a symphysis segment of a jawbone, at least two separating tool guide portions/saw blade guide portions being present at the central component, wherein the improvement is perceived, inter alia, in the fact that between the two separating tool guide portions/saw blade guide portions a positioning aid is provided in order to obtain a spatially correct orientation of the mandibular resection template with respect to the jawbone. In this way, the mandibular resection template can be fastened more exactly and easily than before to the cranial bone, especially to a jawbone, preferably the mandibular bone of the specific patient, so that a high-precision resection of the bone portions to be removed can be performed. Said mandibular resection template can also be claimed separately from the fibula bone material resection and transfer template, viz. without the features of claim 1.

Within the scope of the project according to the invention, ergo also universal templates for resection of the mandible and the fibula have been developed. It was not only intended to achieve significant facilitation and standardization of the clinical intervention of mandibular reconstruction by means of micro-vascular fibula transplant, but also to enforce saving of cost and time vis-à-vis patient-specific resection templates. This was achieved by the configuration according to the invention.

In addition, concerning the resection templates also a plate system design for transplant fixation especially adapted to this technique was developed. Contrary to the current state of the art according to which reconstruction plates are used for bridging a defect or for fixing the transplant, now substantially thinner mini-plates having a profile thickness of 1 mm (1.0 mm) are employed, as, corresponding to the experience gained, they entail a significant advantage in material removal.

Plates such as reconstruction plates (larger than 1 mm in thickness, up to about 3.0 mm) or mini-plates (smaller than or equal to 1 mm in thickness) which may have a framework design, are adapted to the average shape of the mandible and, resp., are pre-shaped to the fibula transplant forming after the separating cut/sawing cut of the resection template. This allows to reach high fitting accuracy and to significantly facilitate transplant fixation.

What is very important is the fact that the mandibular resection template is adapted to the average shape of the mandible. The resection template is as flexible as possible in its adjustment so as to cover a plurality of different resection patterns, in any case the following events, however: triple-segment resection (right mandibular body-front segment-left mandibular body), double-segment resection (right mandibular body including front segment), double-segment resection (left mandibular body including front segment) and single-segment resection. In this way, about 80% of all theoretically possible resections are covered.

In the rear area of the resection template an adaptation in length is enabled which permits to shift the guide slit/saw slit depending on the extent of the defect. The flexible guide slit/saw slit is locked by a basally attached set screw. The set screw preferably is not detachable so as to facilitate handling and to reduce the risk of accident/loss. However, concerning the conditioning of the resection template it is advantageous when the individual parts can be easily dismounted and/or gaps occurring are so large that the medium used for disinfection can have a simple and efficiently cleaning effect.

For performing resection preferably an oscillating saw is used. It is being considered to design the guide slit/saw slit to be about 1 mm in width (+/−0.1 to 0.2 mm) and open to the bottom and/or to the top. Lateral guidance of the saw blade is predetermined in any case.

Primarily, the resection template is intended to be attached in one piece to the mandible. In addition to this, thus even only individual segments are enabled to be attached to the mandible. Via a plug mechanism or a similar connecting constellation, the front segment including the right side or, resp., the front segment including the left side are held to be separable from the remainder.

Integrated bores enable the template to be fixed by means of standard screws having e.g. a diameter of 2.0 mm to the mandible.

An arranged centerline marker in the front segment has an advantageous effect on the orientation and the accurate alignment of the resection template with the mandible. Exact positioning is facilitated.

All detachable components of the resection template are additionally provided with side markers, such as "R" for right-hand and "L" for left-hand. A tumor removal and, resp., resection of the mandible is performed according to anatomic regions (right-hand mandibular body, symphysis, left-hand mandibular body), i.e. when the tumor is located e.g. in the center of the mandibular body, resection will be carried out up to the mandibular angle and up to the symphysis area.

Advantageous embodiments are claimed in the subclaims and hereinafter shall be illustrated in detail.

It is of advantage when the positioning aid is in the form of a notch and bead combination, a notch, a bore, a prism, a color marker, a pin, a screw or a navigation positioning and/or is configured as a positioning fin prepared for contacting a portion of the mandibular bone, such as the symphysis segment.

It is also advantageous when the positioning aid or, resp., the positioning fin projects transversely, preferably orthogonally from the central component. Thus, the orientation of the mandibular resection template is facilitated.

It is useful when the central component is in the form of a frame. Then the view onto the mandible is improved.

The handling capability is improved when the frame has two horizontal webs which are preferably connected to each other at the distal ends thereof via the two separating tool guide portions/saw blade guide portions.

A particular exemplary embodiment is characterized in that the two separating tool guide portions/saw blade guide portions and the two horizontal webs take a rectangular shape at least in a frontal projection. Then the assembly of the individual components is facilitated.

It is also advantageous when the two horizontal webs and the two separating tool guide portions/saw blade guide portions are in the form of a uniform and/or one-piece/integral and/or single-material component or at least one of the separating tool guide portions/saw blade guide portions or both separating tool guide portions/saw blade guide portions is/are a respective part of a displacing component detachable/displaceable/separate from the horizontal webs.

When at least one of the separating tool guide portions/saw blade guide portions has a guide slit/saw slit dimensioned for guiding a bone separating tool, such as a saw blade/a circular saw/a laser or the like, the bone separating tool is prevented from deflecting or tilting.

An especially efficient guidance is achieved when on both sides of the guide slit/saw slit a bone separating tool contact face parallel to the latter is formed.

Accordingly, it is of advantage when the guide slit/saw slit completely protrudes through the material forming the same and, in addition, is configured in extension of its longitudinal extension to be open on one side or on two sides.

The mandibular resection template is especially resistant to break when the material accommodating the guide slit/saw slit is block-shaped, preferably equipped with surfaces (almost) orthogonal to each other, and/or one of the horizontal webs takes a rectangular beam shape, with the horizontal webs being formed e.g. identically in geometry.

It is advantageous when in the area of the positioning fin a marker for the positioning aid is present, such as in the form of a centerline marker, a (through/blind) hole, a projection, an indentation/a recess, a ridge, a groove, a flute or a corrugation. When, for example, a slit is introduced to the mandible, then the ridge can be easily inserted there. By form closure the mandibular resection template then can be precisely orientated. However, also other graphical centerline markers are helpful.

It is advantageous when the marker is in the form of a ridge extending along the longitudinal axis of the fin and having points, for example an acute or triangular cross-section. Although in this case drawbacks have to be expected during manufacture, the orientation of the templates relative to the bone is possible in an especially quick and a non-tiltable manner in such configuration.

The visibility is improved when the marker is present at a front and/or upper side of only one horizontal web or both horizontal webs and/or at the upper side of the positioning fin and/or at the lower side of the central component.

It is worth mentioning that the ridge is present on the upper side of the positioning fin. This allows for efficient handling.

When the positioning fin projects perpendicularly from either of the two horizontal webs, preferably only from the lower one of the two horizontal webs, and preferably also perpendicularly to the two guide slits/saw slits, e.g. as an integral component of the horizontal web, the mandibular resection template can be easily attached from below.

It has proven itself when an extension component adjoins either or each of the two separating tool guide portions/saw blade guide portions on the side facing away from the central component. The space to be treated then can be extended.

It is helpful in this context when the extension component is an integral part of the central component or is a separate extension component adapted to be detachably coupled to a connecting site.

One advantageous exemplary embodiment is also characterized in that the connecting site makes use of two matching coupling geometries which are positively and/or non-positively interacting.

Especially when the one coupling geometry forms a projection and the other coupling geometry forms a matching recess, quick plugging of the individual components can be brought about.

It has proven itself when the coupling geometries interact in a dovetail manner.

One advantageous exemplary embodiment is also characterized in that the recess is formed as a blind hole open at a partial area along its longitudinal axis.

When a bottom of the blind hole defines a stop for the projection, even in stressful situations precise assembly of the single parts of the mandibular template is facilitated.

Also, the resection can be carried out in an especially efficient manner when a plane extending through the guide slits/saw slits takes an angle of about 10° to about 20°, preferably about 12°+/−5° with the upper and lower horizontal struts, when measured on a side facing the mandible.

It is of advantage when the extension component has a circular body from which an extra separating tool guide portion/extra saw blade guide portion projects distally, i.e. at a free end, ergo is present on a side distant from the connecting site.

It has proven itself when in the base body at least one through-hole for receiving a bone screw is provided. The mandibular template is prevented from getting out of place during, or before or after, resection.

In order to enforce proper pulling when screwing the bone screw of the resection template to the mandible, it is advantageous when the through-hole extends diagonally, for example is tilted, with respect to the surface of the base body.

In order to further avoid pivoting, it is of advantage when two through-holes are arranged in parallel to the longitudinal axis of the extension component, advantageously offset against an outer edge of the extension component.

Accordingly, it has proven itself when the through-holes are offset toward the lower outer edge. Preferably, the through-holes are arranged in the lower third of the extension component, however.

More exactly speaking, it is thus useful when the through-holes are ascending from "the front" to "the rear". "The front" in this context is the area which is arranged outside of the patient, whereas "the rear" then is provided on the inside of the patient. "At the bottom", just as "at the top", is defined by the gravity.

When a central axis of a through-hole adopts an angle of about 20°+/−5° with the front or rear substantially vertically orientated surface, the template is pulled tightly matching to the bone when the fastening screws are screwed in.

It has proven itself when the extra separating tool guide portion/extra saw blade guide portion can be removed from the base body, for example via a setting mechanism. Thus, the flexibility of use and, resp., the applications are increased.

When the extra separating tool guide portion/extra saw blade portion has a through-slit between two guide surfaces, even there the precision of the cut to be made can be increased. Preferably, an upper or a lower end of the through-slit then has to be left open.

It has equally proven itself when the extra separating tool portion/extra saw blade portion includes a rod projecting from a block and being adjustably held in an e.g. open channel or a groove.

It is of advantage when the rod can be fixed within the channel via a locking means such as a screw.

Furthermore, it is advantageous when a mandibular bearing block is present at the extension component.

It is desirable when the mandibular bearing block then projects (almost) perpendicularly from the rear surface of the base body or of the extra separating tool portion/extra saw blade portion.

When a slotted hole the longer transverse axis of which is defined by the longitudinal direction of the mandibular hole is formed in the mandibular frame, then easy positioning is enabled while accuracy is still given.

Also, it is of advantage when two extension components are present which are mirror-symmetrical to a center plane, with the center plane being the plane in which the ridge is located and to which the horizontal struts are perpendicular.

One advantageous exemplary embodiment is further characterized in that the central component including its extension components projecting from both ends has such curved shape which (equidistantly) follows the outer contour of an average human mandible.

It is further to be mentioned that, on at least one surface such as the front face, the rod has a corrugation or screening orientated transversely to the longitudinal direction of the rod.

It is of advantage when the mandibular template is (completely) made from metal such as a titanium alloy, or of plastic material such as a polymer.

In this context, e.g. stainless steel, titanium alloys and plastic materials such as ABS plastics are imaginable.

The invention also relates to a method that can be claimed irrespective of the mandibular resection templates or fibula bone material removal and transfer templates. Accordingly, there may be claimed the fact that the mandibular resection template is used to remove bone portions at the mandible and/or the fibula bone material removal and transfer template is used to remove bone from the fibula and/or to transfer, by means of the fibula bone material removal and transfer template, the bones removed from the fibula into the mandibular area and to implant the same there.

As a matter of course, the invention also relates to the combination of the mandibular resection template and the fibula bone material resection and transport template as well as to the use thereof.

BRIEF DESCRIPTION OF THE DRAWINGS

Hereinafter the invention shall be illustrated in detail by way of a drawing in which the different embodiments are shown, wherein:

FIGS. 2 to 5 show the mandibular resection template of FIG. 1 in contact with a mandible in different views (from the front, from the right side, from the left side and from above), each in a slightly perspective view, FIG. 11 shows the fibula bone material resection and transfer template from behind, i.e. from the mandibular side, FIG. 12 shows a further fibula bone material resection and transfer template having a low auxiliary resection bracket, FIG. 13 shows a top view onto the fibula bone material resection and transfer template from FIG. 12 adjacent to a fibula with already performed cuts, FIG. 14 shows the fibula bone material resection and transport template of FIG. 13 with removed residual bone portions, with the bone portions to be transplanted being fastened to the template, FIG. 18 shows the fibula bone material resection and transfer template according to the invention in a transfer position in which the bone pieces to be transplanted are transferred into the shape of the mandibular bone to be replaced or to be repaired, FIGS. 19 to 21 show another view of the fibula bone material resection and transfer template according to the invention in contact with a calf bone/fibula in a front view (FIG. 19), a side view (FIG. 20) and a perspective view (FIG. 21), FIGS. 34 to 38 show the transplanted bones in the mandibular area in different spatial representations (from above, from the front, in a perspective from the front, in a right side perspective and in a left side perspective).

DETAILED DESCRIPTION

Figure 1:
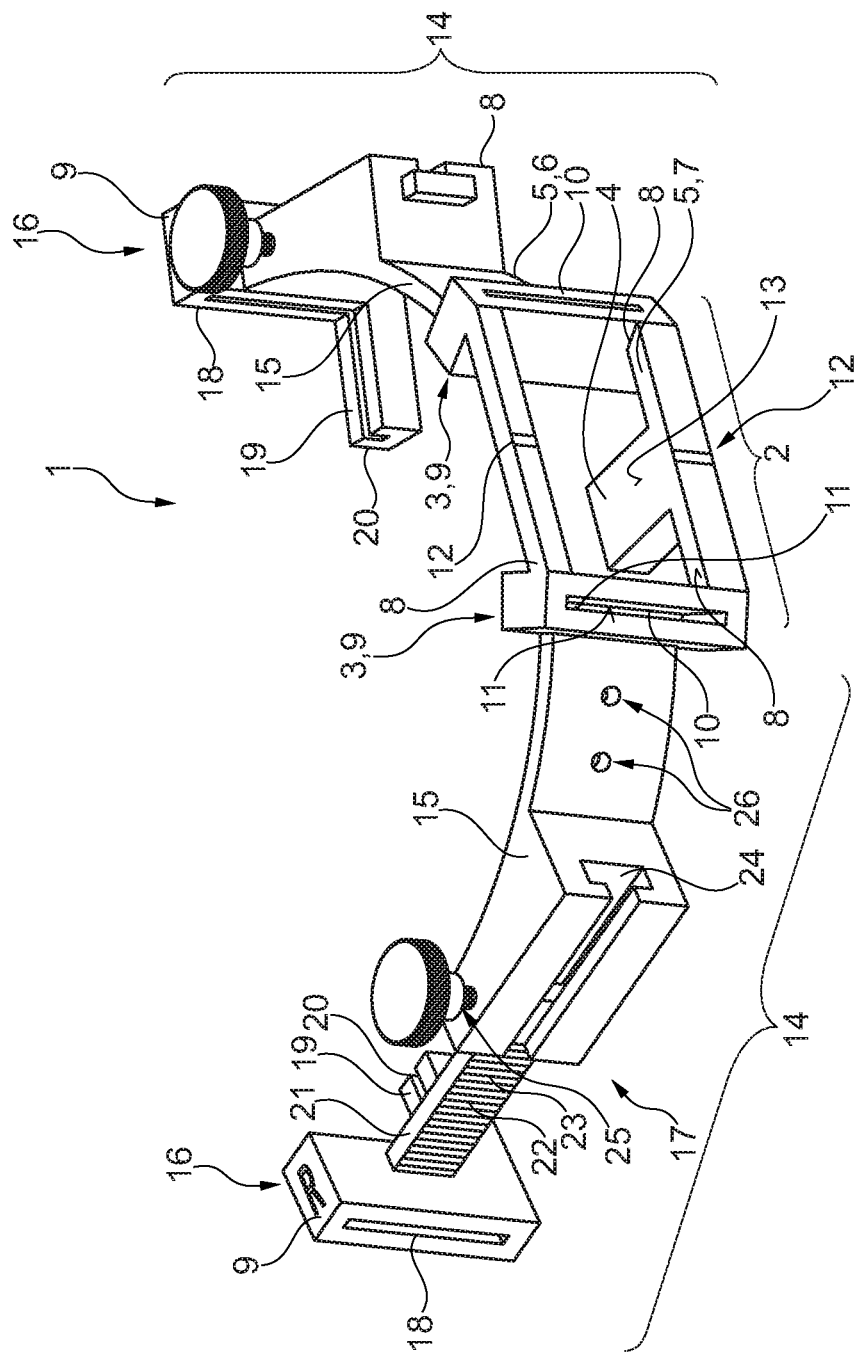
FIG. 1 shows a mandibular resection template according to the invention in a perspective view.
Figure 7:
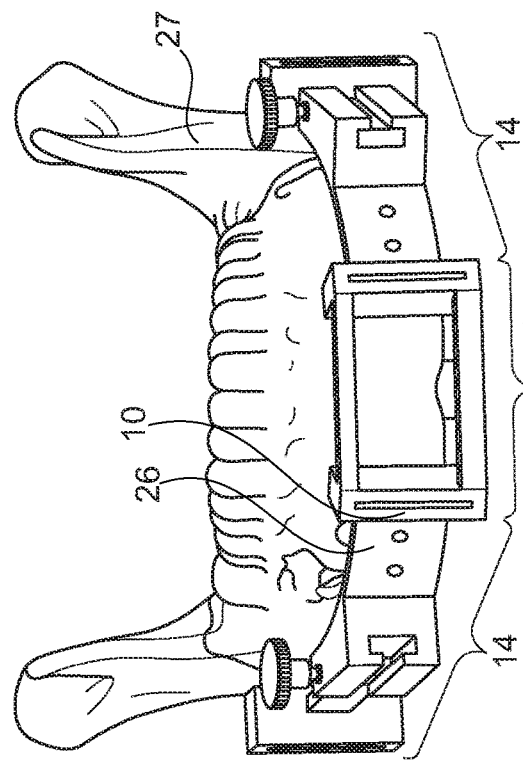
FIGS. 6 to 9 show further representations of different mandibles, similarly to the representations of FIGS. 2 to 5.
Figure 9:
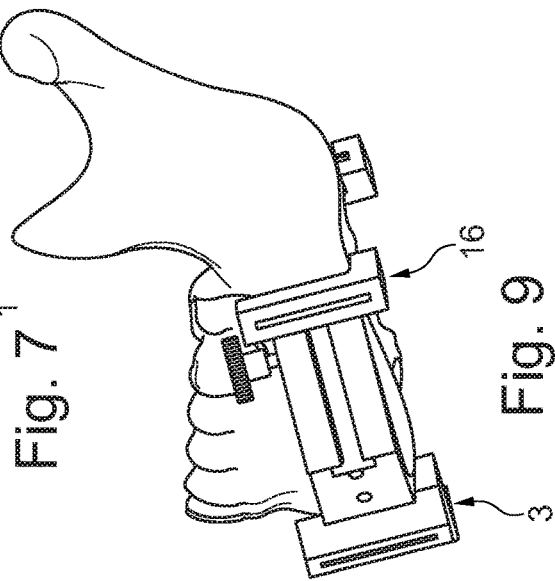
Figure 6:
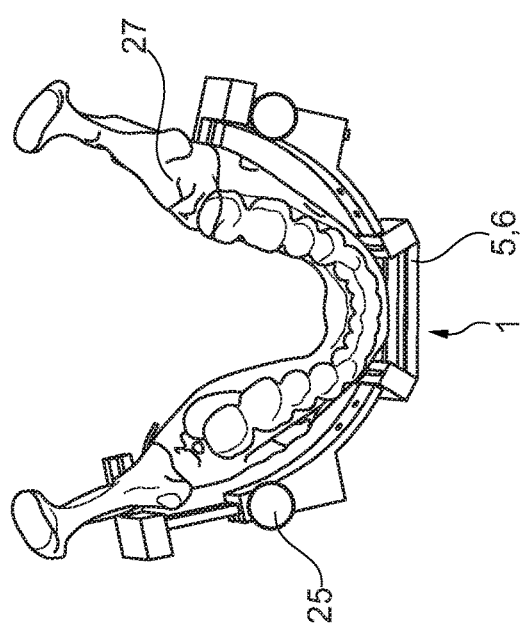
Figure 8:
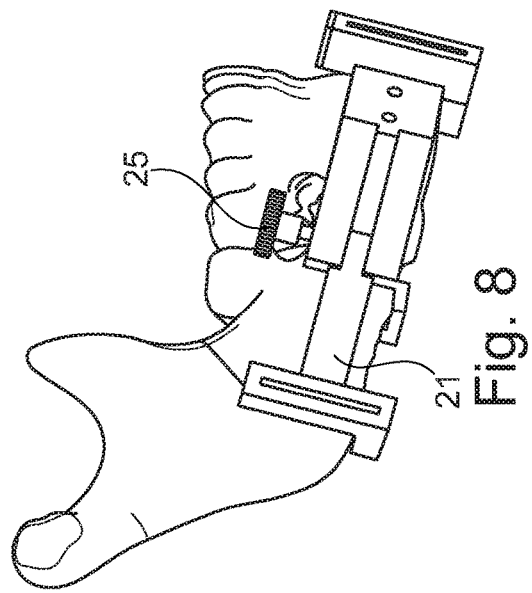

The figures are merely schematic and only serve for the comprehension of the invention. Like elements are provided with like reference numerals. Features of the individual exemplary embodiments may be exchanged for each other.

FIG. 1 illustrates a mandibular resection template 1 according to the invention. The mandibular resection template 1 has a central part/central component 2. Said central component 2 is prepared for being transferred to a symphysis segment of a mandible. The central component 2 includes at both outer ends, with the ends defining the longitudinal axis, two separating tool guide portions/saw blade guide portions 3. Between the two separating tool guide portions/saw blade guide portions 3 a positioning fin 4 is present. The separating tool guide portions need not contact a separating tool, whereas the saw blade guide portions comparable thereto are definitely provided for physically contacting a separating tool such as a milling cutter, a saw blade or any other metallic machining tool. The positioning aid does not necessarily have to enter into physical contact with or even abut on the bone, but may use, for example, only optical means for orientation. When configuring the positioning aid as a positioning fin, physical contacting of the bone is desirable, however. Said positioning aid/positioning fin 4 is not absolutely necessary for particular embodiments of the invention.

The positioning fin 4 in any case projects perpendicularly on a plane across the central component 2 from a horizontal web 5 in the direction of the mandible. There is an upper horizontal web 6 and a lower horizontal web 7. The positioning fin 4 projects from the lower horizontal web 7. In the present exemplary embodiment, it is plate-shaped, but it may as well be pin-shaped, for example having a circular, elliptic or polygonal cross-section.

At the distal ends 8 of the horizontal webs 5 the separating tool guide portions/saw blade guide portions 3 are arranged in one piece and in one material in the form of blocks 9. In the blocks 9 guide slits/saw slits 10 are provided. One guide slit/saw slit 10 is provided for each separating tool guide portion/saw blade guide portion 3. The guide slit/saw slit 10 is located between two vertically aligned bone separating tool contact faces 11 extending in parallel to each other.

At the front and/or at the bottom of the lower horizontal web 7 a marker 12 is formed as a centerline marker, just as at the front and/or at the top of the upper horizontal web 6.

Instead of the centerline marker, also on the surface 13 of the positioning fin 4 facing the upper horizontal web 6 a ridge (not shown) extending in the longitudinal direction of the positioning fin 13, viz. from the lower horizontal web 7 toward the mandible, can be attached. Said ridge then may engage in a notch introduced to the bone and may act in a positioning manner.

One extension component 14 projects from both sides of the central component 2. The two extension components 14 are designed as integral parts of the central component 2 here. However, one extension component 14 or both extension components 14 may also be detachably coupled to the central component 2, viz. on the outside of each block 9. For this purpose, appropriate connecting sites having coupling geometries such as projections and recesses, for example in the form of dovetail configurations, can be designed, for example while forming a bottom and a stop.

In any case, each extension component 14 includes a base body 15 at each end of which an extra saw blade guide portion 16 is present. A setting mechanism 17 is used to safeguard displaceability of the extra separating tool guide portion/extra saw blade guide portion 16 in the form of a further block from the base body 15. In the block-type extra separating tool guide portions/extra saw blade guide portions 16, too, through-slits 18 are present which are configured similarly or identically to the slits/saw slits 10 in the separating tool guide portions/saw blade guide portions 3.

A mandibular bearing block 19 having a slotted hole projects from the ends of the base body 15, e.g. in the area of the setting mechanism 17, or else from the extra separating tool guide portions/extra saw blade guide portions 16. The slotted hole is not shown. In the exemplary embodiment presented here, a slit extension 20 is used instead. The slotted hole may thus replace the slit extension 20, the longitudinal axis of the slotted hole configured as a through-hole is preferably orientated in the direction of the slit of the slit extension 20.

The setting mechanism includes a rod 21 on the front face/front surface 22 of which a corrugation 23 is provided. The rod 21 engages in a channel 24 of open design and is detachably held in position by a locking means 25 in the form of a set screw. In each extension component 14 there are at least two through-holes 26 for securing the mandibular resection template 1 by means of screws to the mandible not shown here.

In FIGS. 2 to 9, the mandibular resection template according to the invention is shown in different positions at a mandible 27.

In FIGS. 10 to 38, hereinafter the attention will increasingly be drawn to a fibula bone material resection and transfer template according to the invention and, resp., to the bone resected from a fibular bone and to bone pieces to be transplanted into the mandible.

Figure 10:
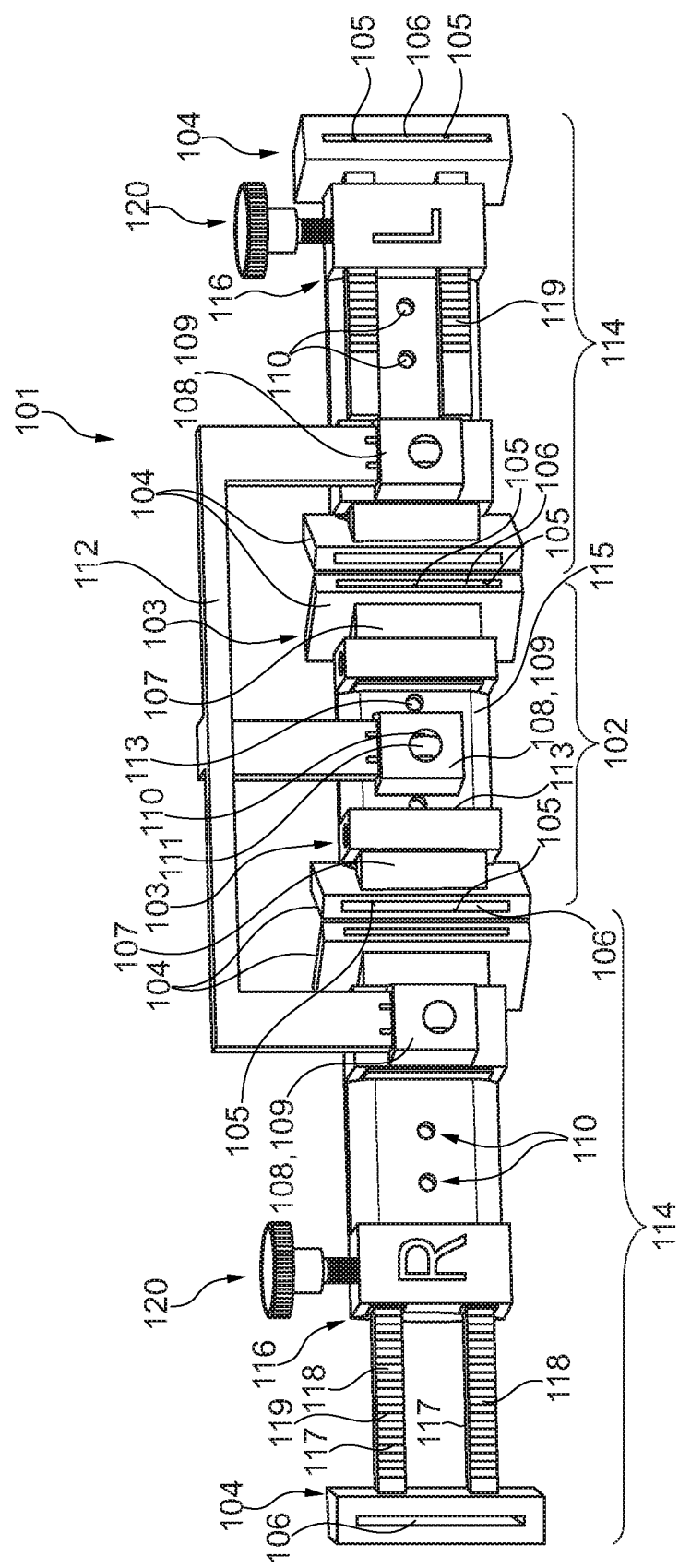
FIG. 10 shows a perspective view of a fibula bone material resection and transfer template according to the invention.

For example, in FIG. 10 a fibula bone material resection and transfer template 101 according to the invention is illustrated. Said fibula bone material resection and transfer template 101 includes a central part 102. At each of the distal ends 103 thereof a bone separating tool guide portion 104 is present. Said bone separating tool guide portions 104 may be in the form of jaws or blocks and either may be connected integrally with the central part and, resp., a base body of the central part 102 or may be movably coupled thereto. At least one of the bone tool guide portions 104 should be mounted so that it can be moved away and pushed close.

Each bone separating tool guide portion 104 includes a guide slit 106 between two vertical faces 105. Said guide slits 106 are open/permeable on the front and rear sides. Each guide slit 106 is completely surrounded by material except for the elongate openings in the front and rear sides. However, a guide slit 106 may be open at the bottom and/or at the top.

For displaceability of a bone separating tool guide portion 104 it is suitable to provide a beam 107. The beam 107 is movably supported in a guide path encompassing the same. A fixing screw may be used for securing the beam 107.

In the middle of the central part 102 a bracket receiving device 108 is located. The bracket receiving device 108 is a clip 109 here and has a through-hole 110 into which a convex spring portion 111 of an auxiliary resection bracket 112 engages. On the left and on the right of the clip 109 respective receiving holes 113 are provided to receive a bone screw by means of which attachment to a fibula bone can be implemented. The receiving holes 113 are configured in the form of bores.

On both sides of the central part 102 a respective supplementary component 114 adjoins. Between the supplementary component 114 a central body 115 of the central part 102 is thus arranged.

Each supplementary component 114 includes a further bone separating tool guide portion 104. Each of said bone separating tool guide portions 104 of the supplementary components 114 then is maintained to be displaceable via a displacing mechanism 116. Accordingly, two respective guiding webs 117 are used both of which have ribs, notches or stops on their front side 118 so as to form a screening 119. In turn, bracket receiving devices 108 in the form of clips 109 are provided into which ends of the auxiliary resection bracket 112 engage. The connection between the auxiliary resection bracket 112 and the clips 109 is configured to be similar or identical to the one described already before.

In each of the supplementary components 114 equally through-holes 110 are provided to enable securing to bones via screws. The auxiliary resection bracket 112 is detachable for fixing the template. Set screws 120 are used for fixing the flexible slit.

While in FIG. 10 the fibula bone material resection and transfer template is shown substantially from the front, in FIG. 11 it is represented substantially from the rear, i.e. when viewed from the fibular bone. Hence the rear side is visible. The length of the supplementary components 114 preferably should be variable between 45.2 mm and 66.2 mm. The sequential length of the central part 102 preferably should be 30 mm and may be fixed.

Figure 15:
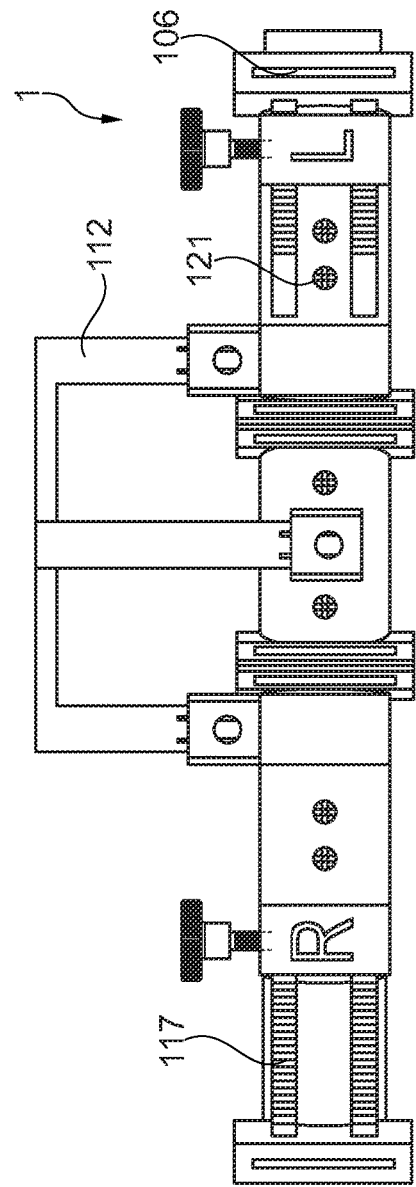
FIGS. 15 to 17 show a second embodiment of a fibula bone material resection and transfer template comprising a higher auxiliary resection bracket and blocks jointly receiving plural slits, with FIG. 15 corresponding to the view of FIG. 12 and FIG. 16 corresponding to a view of FIG. 13 as well as FIG. 17 corresponding to a view of FIG. 14.
Figure 16:
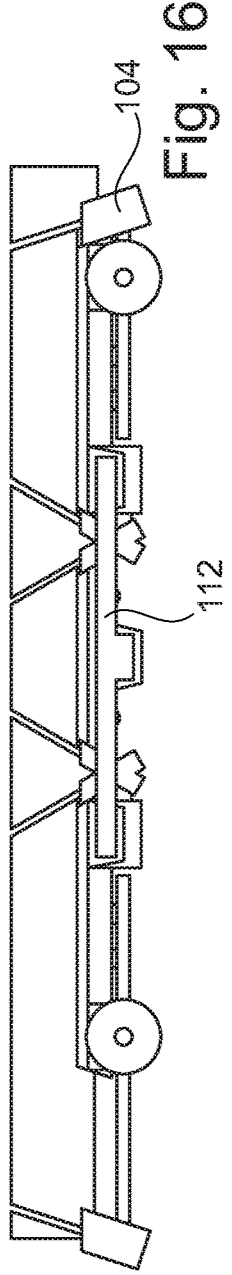
Figure 17:
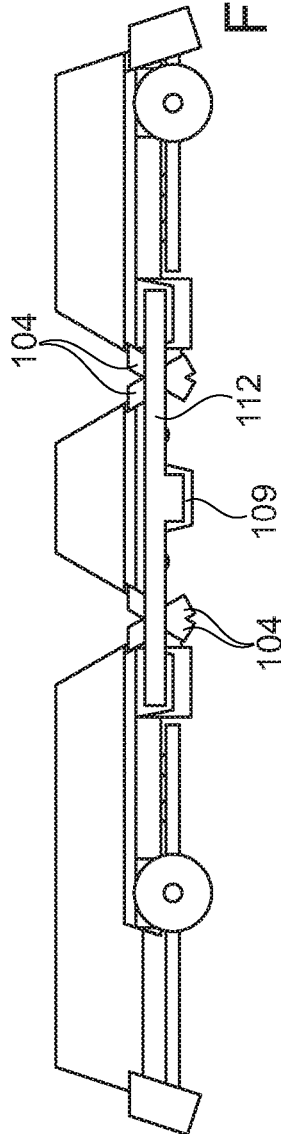
Figure 22:
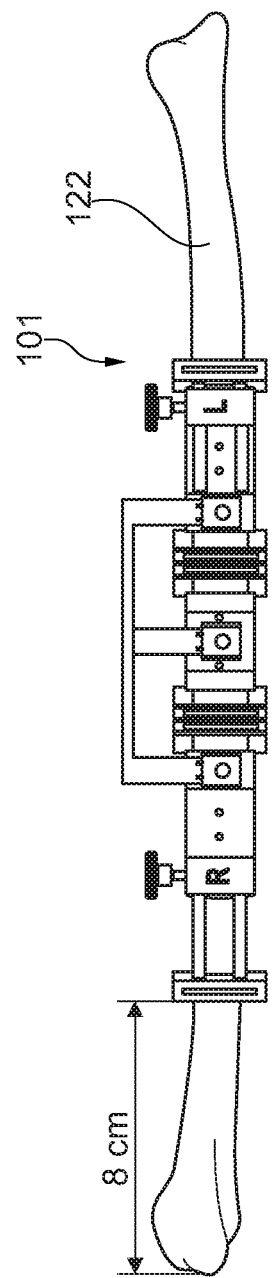
FIGS. 22 to 24 show another view of the fibula bone material resection and transfer template attached to the fibula bone in plural forms of representation corresponding to FIGS. 19 to 21, with the bones to be resected being shown.
Figure 23:
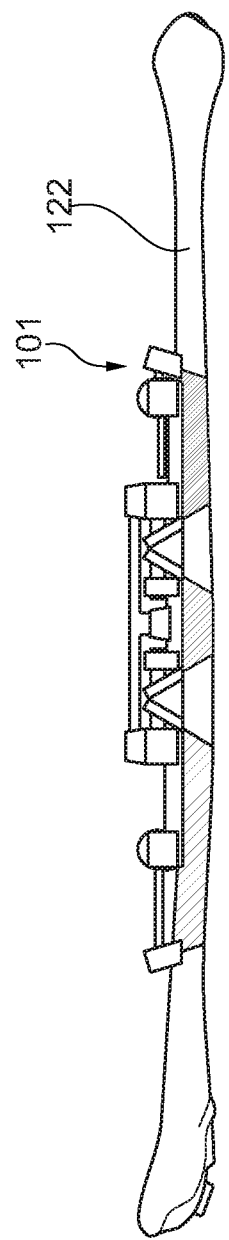
Figure 24:
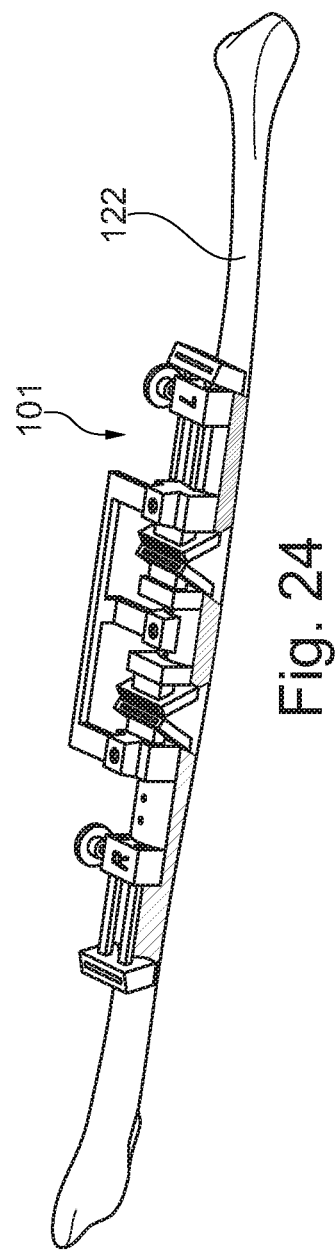
Figure 25:
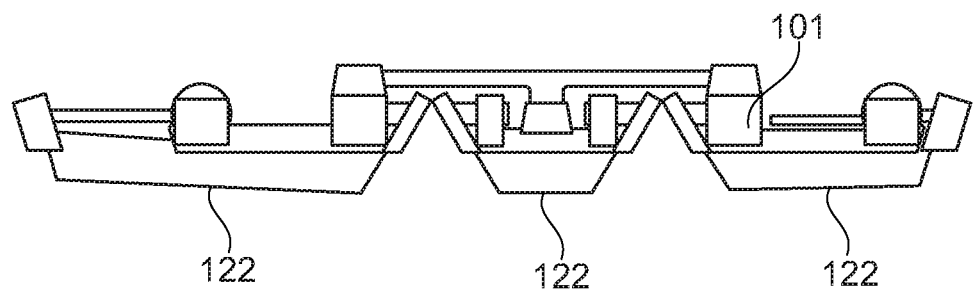
FIGS. 25 to 27 show the resected bone pieces at the attached fibula bone material resection and transfer template in forms of representation comparable to FIGS. 22 to 24, FIGS. 28 to 30 show the auxiliary implanting bracket which is geometrically modified vis-à-vis the first auxiliary resection bracket and by means of which the resected bone pieces are brought into a shape similar to the mandible and thus are prepared for being transplanted.
Figure 26:
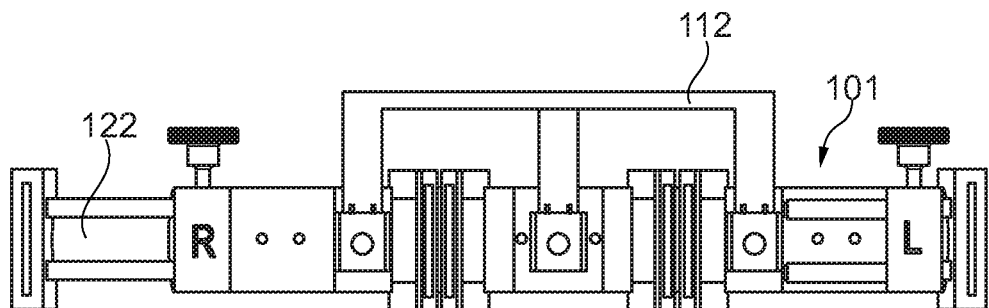
Figure 27:
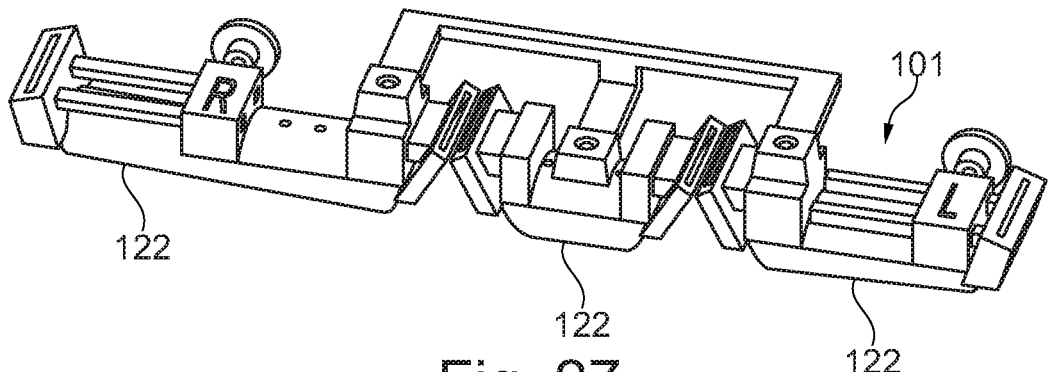
Figure 28:
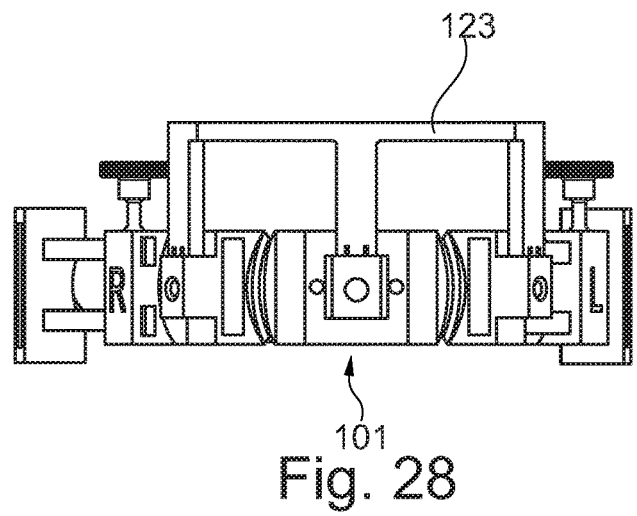
Figure 29:
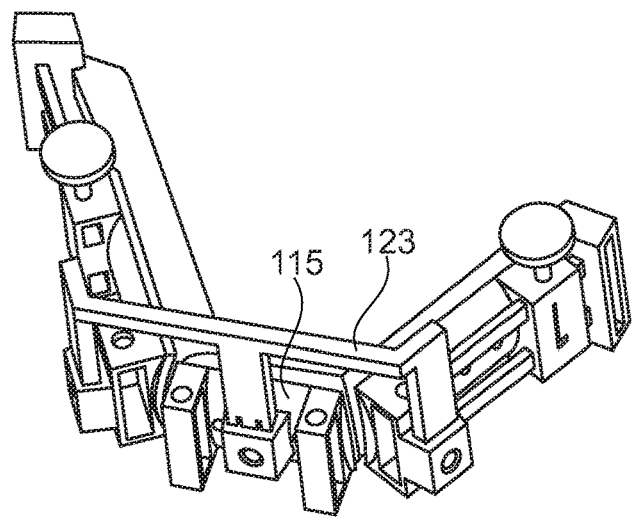
Figure 30:
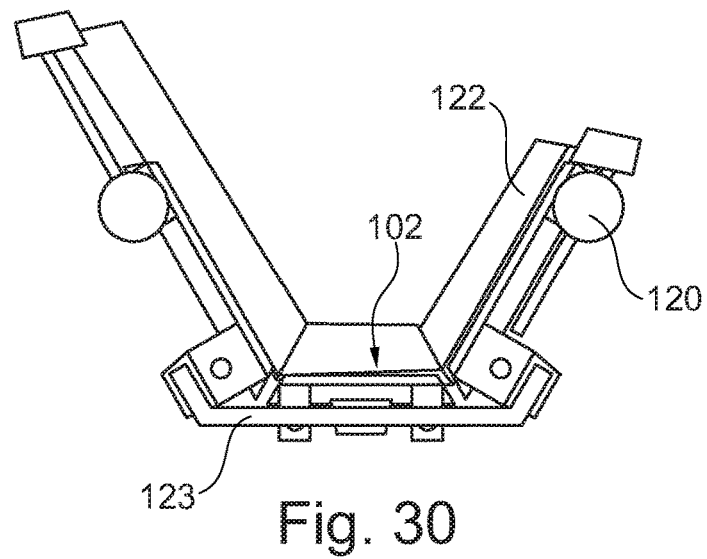
Figure 31:
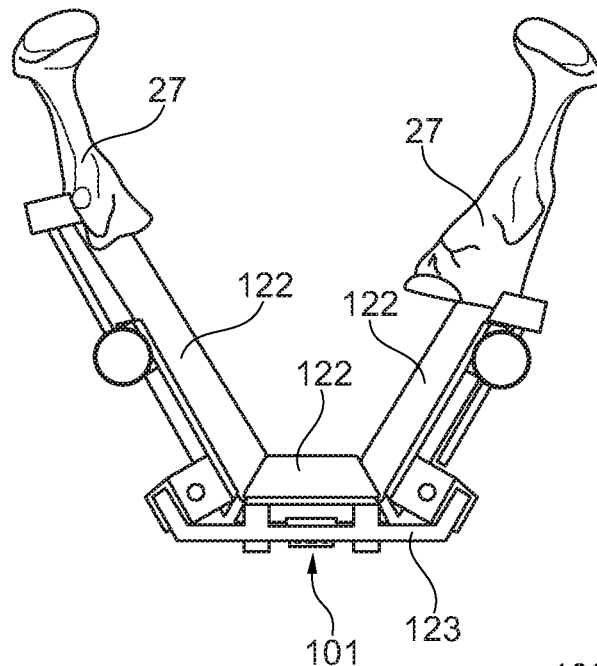
FIGS. 31 to 33 show the fibula bone pieces brought into position in the state inserted in the remaining mandible in a top view, a front view and a perspective view.
Figure 33:
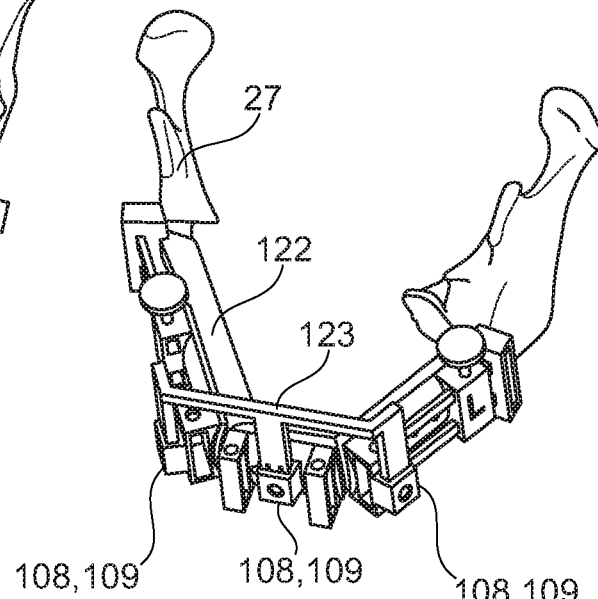
Figure 32:
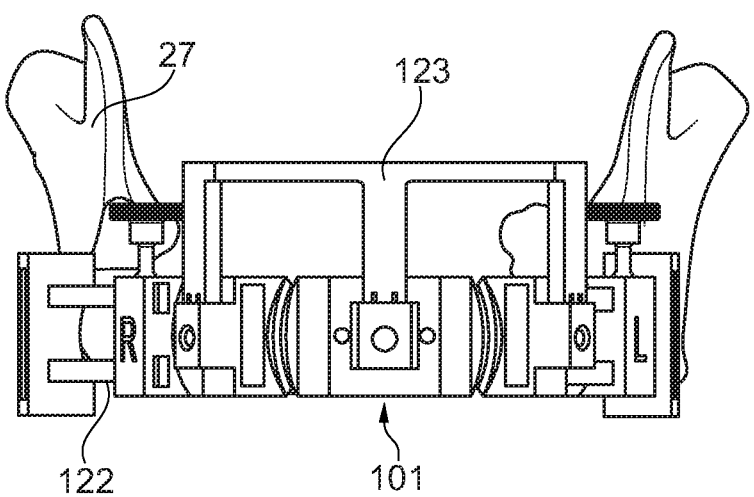

In FIGS. 12 and 15 already bone screws 121 are inserted so as to obtain, as in FIGS. 13 and 14 and 16 as well as 17, the securing to parts of a fibular bone 122. In FIG. 18 an auxiliary implanting bracket 123 which is slightly different in geometry from the auxiliary resecting bracket 112 is used. The individual portions of the fibular bone 122 then are completely newly arranged, in the spatial position similarly as predefined by the mandibular resection template 1, and preferably identically. The distally outermost bone separating tool guide portions 104 have been removed. This is also true for the bone separating tool guide portions 104 of the central part 102. The saw slits or, resp., guide slits 106 were removed so as to be able to set the segments "to be abutting".

The operation of attaching, cutting and resecting as well as of subsequent assembling can be clearly inferred from FIGS. 19 to 38.

It should be apparent that the foregoing relates only to the preferred embodiments of the present application and the resultant patent. Numerous changes and modification may be made herein by one of ordinary skill in the art without departing from the general spirit and scope of the invention as defined by the following claims and the equivalents thereof.

LIST OF REFERENCE NUMERALS 1 mandibular resection template
2 central part/central component
3 separating tool guide portion/saw blade guide portion
4 positioning aid/positioning fin
5 horizontal web
6 upper horizontal web
7 lower horizontal web
8 distal end of horizontal web
9 block
10 saw slit
11 separating tool contact face
12 marker
13 surface of positioning fin
14 extension component
15 base body
16 extra separating tool guide portion/extra saw blade guide portion
17 setting mechanism
18 through-slit
19 mandibular bearing block
20 slit extension
21 rod
22 front surface
23 corrugation
24 channel
25 locking means
26 through-hole
27 mandible 101 fibula bone material removal and transfer template
102 central part
103 end
104 bone separating tool guide portion
105 vertical face
106 guide slit
107 beam
108 bracket receiving device
109 clip
110 through-hole
111 spring portion
112 auxiliary resection bracket
113 receiving hole
114 supplementary component
115 central body
116 displacing mechanism
117 guiding web
118 front side
119 screening
120 set screw
121 bone screw
122 fibular bone
123 auxiliary implanting bracket

We claim:

1. A fibula bone material removal and transfer template comprising:
   a center part with a central body configured to be attached to a fibula by screws,
   wherein each end of the central body has a bone separating tool guide portion configured to accept a saw blade therethrough for cutting the fibula,
   wherein at least one of the bone separating tool guide portions is mounted such that it can translate away from the center part along a beam,
   wherein the beam, movably supported in a guide path, extends from at least one of the bone separating tool guide portions of the central body separate from the center part,
   a supplementary component on either or each of the bone separating tool guide portions on a side facing away from the central body, the supplementary component configured to be attached to the fibula by screws and configured to accept a saw blade therethrough for cutting the fibula,
   and
   an auxiliary resection bracket being removably received in a bracket receiving device of the center part and in a bracket receiving device of the supplementary component,
   wherein the fibula bone material removal and transfer template is configured to be used to facilitate bone removal from the fibula and subsequent implantation of the removed fibula bone into a mandibular area of a patient.

2. The fibula bone material removal and transfer template according to claim 1,
   wherein at least one of the bone separating tool guide portions of the central body has a guide slit formed between two vertical surfaces which is open on a front side and a rear side thereof, the guide slit configured to accept the saw blade therethrough.

3. The fibula bone material removal and transfer template according to claim 2,
   wherein the guide slit is configured to be open on a lower side or on an upper side thereof.

4. The fibula bone material removal and transfer template according to claim 1, wherein a fixing screw for securing the beam protrudes into the guide path.

5. The fibula bone material removal and transfer template according to claim 1, wherein the bracket receiving device of the center part comprises a hole configured to lockingly receive a spring portion fixed to the auxiliary resection bracket.

6. The fibula bone material removal and transfer template according to claim 1, wherein the bracket receiving device of the center part is a clip and on a left hand side and on a right hand side of the clip a receiving hole configured to receive a bone screw is provided.

7. The fibula bone material removal and transfer template according to claim 6, wherein the receiving hole has an axis of symmetry which is orientated transversely to a central plane extending through the central body.

* * * * *